United States Patent
Oguro et al.

(10) Patent No.: US 11,166,918 B2
(45) Date of Patent: Nov. 9, 2021

(54) LOW-SUBSTITUTED HYDROXYPROPYL CELLULOSE AND SOLID PREPARATION

(71) Applicant: Shin-Etsu Chemical Co., Ltd., Tokyo (JP)

(72) Inventors: Tsubasa Oguro, Niigata (JP); Yasuyuki Hirama, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 16/993,375

(22) Filed: Aug. 14, 2020

(65) Prior Publication Data

US 2021/0046012 A1    Feb. 18, 2021

(30) Foreign Application Priority Data

Aug. 16, 2019   (JP) .............................. JP2019-149384

(51) Int. Cl.
*A61K 9/20* (2006.01)

(52) U.S. Cl.
CPC .......... *A61K 9/2054* (2013.01); *A61K 9/2072* (2013.01); *A61K 9/2095* (2013.01)

(58) Field of Classification Search
CPC ... A61K 9/2054; A61K 9/2072; A61K 9/2095
See application file for complete search history.

(56) References Cited

U.S. PATENT DOCUMENTS

| 2018/0100027 A1 | 4/2018 | Hirama et al. |
| 2018/0100029 A1 | 4/2018 | Hirama |

FOREIGN PATENT DOCUMENTS

| JP | 2018062653 | 4/2018 |
| JP | 2018062654 | 4/2018 |

*Primary Examiner* — Robert A Wax
*Assistant Examiner* — Olga V. Tcherkasskaya
(74) *Attorney, Agent, or Firm* — Myers Bigel, P.A.

(57) ABSTRACT

There is provided low-substituted hydroxypropyl cellulose (L-HPC) having good bindability, anti-capping performance and disintegratability. More specifically, there are provided L-HPC having a hydroxypropoxy group content of 5 to 16% by mass and a volume fraction of long fibrous particles of more than 50.0% relative to all of L-HPC particles which are classified, on a basis of dynamic image analysis, into fine particles, spherical particles, the long fibrous particles and short fibrous particles; and a solid preparation containing the L-HPC.

12 Claims, 1 Drawing Sheet

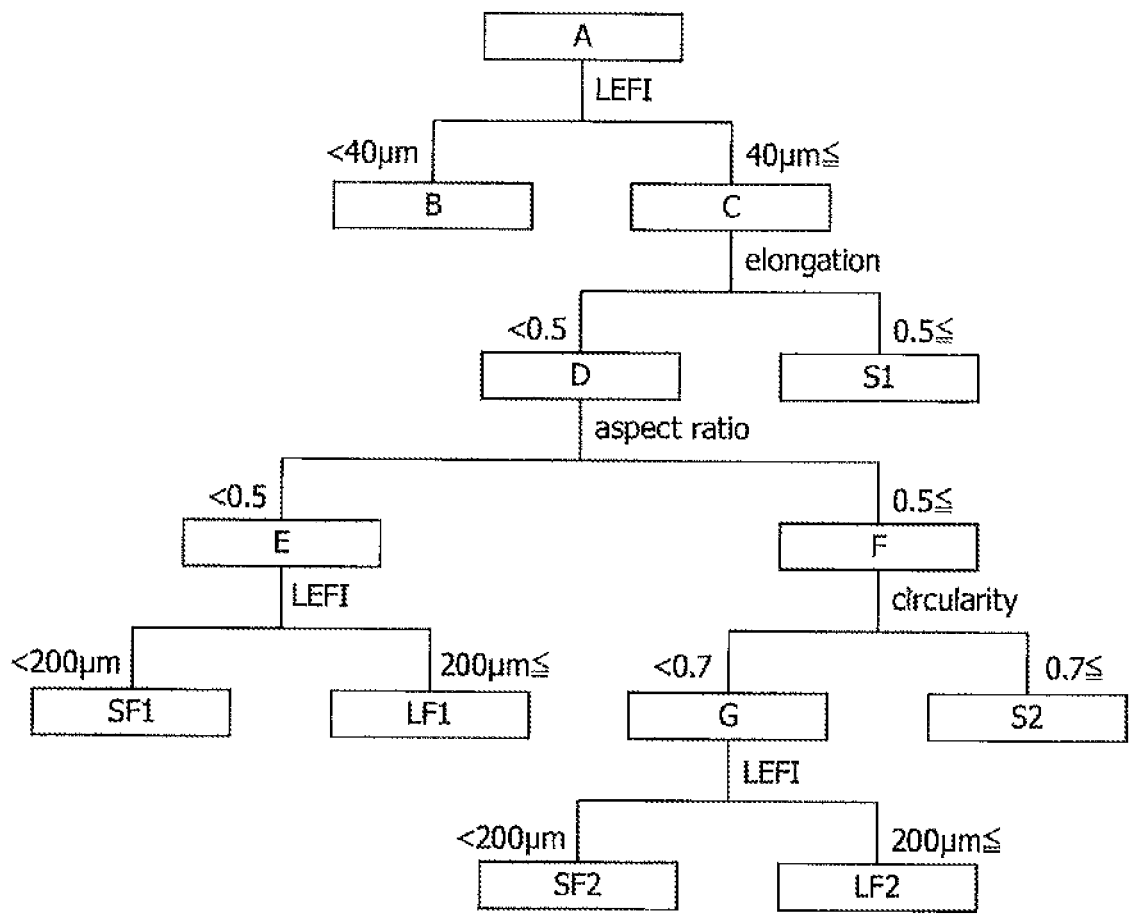

LOW-SUBSTITUTED HYDROXYPROPYL CELLULOSE AND SOLID PREPARATION

CROSS-REFERENCE TO RELATED APPLICATION

This U.S. nonprovisional application claims priority to Japanese Application No. 2019-149384 filed Aug. 16, 2019, the entire contents of which are incorporated herein by reference.

BACKGROUND OF THE INVENTION

1. Field of the Invention

The invention relates to low-substituted hydroxypropyl cellulose which is contained as a binder or a disintegrant by a solid preparation in the pharmaceutical or food field; and the solid preparation.

2. Related Art

A solid preparation used as, for example, pharmaceuticals or health food, disintegrates as a result of water absorption and swelling of the disintegrant contained in the solid preparation. Examples of the disintegrant include low-substituted hydroxypropyl cellulose (hereinafter, also described as "L-HPC"), carboxymethyl cellulose, carboxymethyl cellulose calcium salt, starch, and starch derivatives.

Especially in the field of pharmaceuticals, unstable drugs increase among newly developed drugs, and available additives also are limited from the viewpoint of drug interaction. In these circumstances, L-HPC has been widely used as a nonionic disintegrant or binder, and can be said to be a preferable additive.

A tablet, which is one of the solid dosage forms of pharmaceuticals or foods, is obtained by compression-molding a powder into a certain shape, and has advantages such as easy handling. The tablet is most commonly used, and occupies about 50% in the total amount of production in the pharmaceutical field.

Examples of the method for producing a tablet include a city direct tableting, a dry granulation tableting, an extrusion granulation tableting, and a wet granulation tableting.

The dry direct tableting is a method of directly tableting a mixture of a drug and an excipient or the like to obtain a tablet. The dry direct tableting has an advantage in that the steps of granulation, drying and size regulation can be omitted in comparison with a wet granulation tableting, so that production steps are simple and production cost can be greatly reduced. On the other hand, problems such as uniformity of drug content, weight variation between tablets, and tableting failure, tend to occur more easily than the wet granulation tableting.

The tableting failure is a trouble in the step of tableting, and typical examples thereof include sticking, binding, and capping. In particular, the capping is a phenomenon in which a tablet is peeled off into a cap shape, and is also seen during coating, packing and transporting a tablet. It is necessary to suppress the capping because the drug content is lowered in addition to unusual appearance. In order to prevent capping, addition of low-substituted hydroxypropyl cellulose (JP 2018-062653A) having a hydroxypropoxy group content of 5 to 16% by mass, a volume fraction of long fibrous particles of 15 to 50%, and a volume fraction of short fibrous particles of 23 to 60%, or addition of low-substituted hydroxypropyl cellulose (JP 2018-062654A) having a hydroxypropoxy group content of 5 to 16% by mass, a volume fraction of long fibrous particles of 20 to 40%, a volume fraction of short fibrous particles of 26 to 60%, and the volume fraction of short fibrous particles which is larger than the volume fraction of long fibrous particles has been proposed, when all particles of low-substituted hydroxypropyl cellulose are divided into fine particles, spherical particles, and fibrous particles consisting of long and short fibrous particles.

SUMMARY OF THE INVENTION

However, when L-HPC described in JP 2018-062653A or JP 2018-062654A is used in a dry direct tableting or the like at a low dosage, there is room for improvement because there are cases in which capping takes place due to insufficient bindability.

In view of the above circumstances, an object of the invention is to provide low-substituted hydroxypropyl cellulose having good bindability, anti-capping performance and disintegratability.

As a result of extensive studies to achieve the above object, the inventors have found that L-HPC having a controlled content of fibrous particles, particularly long fibrous particles, exhibits good bindability, anti-capping performance and disintegratability, and have arrived at the invention.

In an aspect of the invention, there is provided low-substituted hydroxypropyl cellulose having a hydroxypropoxy group content of 5 to 16% by mass and a volume fraction of long fibrous particles of more than 50.0% relative to all of low-substituted hydroxypropyl cellulose particles, the all of low-substituted hydroxypropyl cellulose particles being classified, on a basis of dynamic image analysis, into fine particles, spherical particles, the long fibrous particles and short fibrous particles;
wherein
the fine particles have a length of fiber of less than 40 μm;
the spherical particles have a length of fiber of 40 μm or more and consist of first and second spherical particles, wherein the first spherical particles have an elongation, which is a ratio of a diameter of fiber to a length of fiber, of 0.5 or more, and the second spherical particles have an elongation of less than 0.5, an aspect ratio, which is a ratio of a minimum Feret diameter to a maximum Feret diameter, of 0.5 or more, and a circularity, which is a ratio of a perimeter ($P_{EQPC}$) of a circle that has the same area as a projection area of a particle to a real perimeter ($P_{real}$) of a particle, of 0.7 or more;
the long fibrous particles have a length of fiber of 200 μm or more and an elongation of less than 0.5, and consist of first and second long fibrous particles, wherein the first long fibrous particles have an aspect ratio of less than 0.5, and the second long fibrous particles have an aspect ratio of 0.5 or more and a circularity of less than 0.7; and
the short fibrous particles have a length of fiber of 40 μm or more and less than 200 μm and an elongation of less than 0.5, and consist of first and second short fibrous particles, wherein the first short fibrous particles have an aspect ratio of less than 0.5, and the second short fibrous particles have an aspect ratio of 0.5 or more and a circularity of less than 0.7.

In another aspect of the invention, there is also provided a solid preparation comprising the low-substituted hydroxypropyl cellulose.

According to the invention, there can be produced a high-quality solid preparation having good bindability, anti-capping performance and disintegratability. Further, even a low content of L-HPC can provide the solid preparation with good bindability, anti-capping performance and disintegratability, so that the content of the components other than L-HPC in the solid preparation can be increased in comparison with those in the conventional solid preparations, or the size of tablet can be made smaller.

BRIEF DESCRIPTION OF THE DRAWING

FIG. 1 shows a flow chart of dividing "all particles" of L-HPC into four types of particles: "fine particles", "long fibrous particles (LF1 and LF2)", "short fibrous particles (SF1 and SF2)", and "spherical particles (S1 and S2)".

DETAILED DESCRIPTION OF THE PREFERRED EMBODIMENTS

First, L-HPC will be described.

In this specification, L-HPC particles are divided into four types of particles: "long fibrous particles", "short fibrous particles", "spherical particles" and "fine particles". FIG. 1 shows a flowchart summarizing the method of dividing "all particles" of L-HPC into four types of particles: "fine particles", "long fibrous particles (LF1 and LF2)", "short fibrous particles (SF1 and SF2)" and "spherical particles (S1 and S2)".

A volume fraction of each type of L-HPC particles can be calculated by measuring the shape parameters such as a length of fiber (LEFI), a diameter of fiber (DIFI), an elongation, an aspect ratio and a circularity based on a dynamic-image analysis. The dynamic image analysis is a method in which images of particles dispersed in a fluid such as a gas or a solvent are continuously photographed and are binarized and analyzed to obtain a particle diameter or a particle shape. The analysis may be performed by using, for example, a dynamic-image analysis type particle diameter distribution analyzer, QICPIC/R16 (manufactured by Sympatec GmbH).

All particles A are divided into particles C having a length of fiber (LEFI) of 40 μm or more and fine particles B having a length of fiber of less than 40 μm. The LEFI is defined as the length of the longest direct path that connects the ends of the particle within the contour of the particle. A QICPIC/R16 equipped with an M7 lens has a detection limit of 4.7 μm, and thus fails to detect a particle of an LEFI of less than 4.7 μm. However, the volume of the particles having an LEFI of less than 4.7 μm is extremely small relative to that of all particles of L-HPC, so that it is negligible for the purposes of the invention.

The particles C having an LEFI of 40 μm or more are divided into first spherical particles (S1) having an elongation of 0.5 or more and particles D having an elongation of less than 0.5, wherein the elongation is a ratio (DIFI/LEFI) of a diameter of the fiber (DIFI) to LEF of the particle. The DIFI is defined as the minor diameter of a particle, and is calculated by dividing the projection area of the particle by the sum of all lengths of the fiber branches of the particle.

The particles D having an LEFI of 40 μm or more and an elongation of less than 0.5 are divided into particles E having an aspect ratio of less than 0.5 and particles F having an aspect ratio of 0.5 or more, wherein the aspect ratio is a ratio (Fmin/Fmax) of the minimum Feret diameter (Fmin) to the maximum Feret diameter (Fmax). Each particle has an aspect ratio of more than 0 and not more than 1. The Feret diameter is the distance between two parallel tangent lines that put the particle therebetween. The maximum Feret diameter (Fmax) is the largest distance between pairs of tangent lines to the particle in consideration of all possible orientations by changing the directions from 0° to 180°, and the minimum Feret diameter (Fmin) is a minimum distance between pairs of tangent lines to the particle in consideration of all possible orientations by changing the direction from 0° to 180°.

The fibrous particles E having an LEFI of 40 μm or more, and an elongation of less than 0.5, and an aspect ratio of less than 0.5 are divided into first long fibrous particles (LF1) having an LEFI of 200 μm or more and first short fibrous particles (SF1) having an LEFI of less than 200 μm.

The particles F having an LEFI of 40 μm or more, and an elongation of less than 0.5, and an aspect ratio of 0.5 or more are divided into second spherical particles (S2) having a circularity of 0.7 or more and fibrous particles G having a circularity of less than 0.7. The circularity is a ratio of the perimeter ($P_{EQPC}$) of a circle that has the same area as the projection area ($A_P$) of the particle to the real perimeter ($P_{real}$) of the particle, and is defined by the following equation. Each particle has a circularity of more than 0 and not more than 1. A particle having a smaller circularity has a more irregular shape. The EQPC is the diameter of a circle of an equal projection area, and is defined as the diameter of a circle that has the same area as the projection area of the particle, and is also called Heywod diameter.

$$\text{Circularity} = P_{EQPC}/P_{real} = 2\sqrt{\pi \cdot A_P}/P_{real}$$

The fibrous particles G having an LEFI of 40 μm or more, an elongation of less than 0.5, an aspect ratio of 0.5 or more, and a circularity of less than 0.7 are divided into second long fibrous particles (LF2) having an LEFI of 200 μm or more and second short fibrous particles (SF2) having an LEFI of less than 200 μm.

The volume ($V_m$) of the fine particles of L-HPC may be calculated by the following equation where each fine particle is assumed to be a sphere having a diameter of EQPC.

$$V_m = (\pi/6) \times (EQPC)^3 \times N_m,$$

wherein $N_m$ is the number of fine particles in a sample, and EQPC is a median EQPC corresponding to the 50% cumulative value on a number-based cumulative particle diameter distribution curve of fine particles.

In the specification, particles having an LEFI of 40 μm or more, which are particles other than the fine particles having an LEFI of less than 40 μm among all of the particles, are divided into "long fiber particles", "short fiber particles", and "spherical particles", which are distinguished from each other. This division or classification is based the above shape parameters of particles including LEFI, an elongation, an aspect ratio and a circularity.

<Long Fibrous Particles>

Particles satisfying the following definition of LF1 or LF2 are divided into "long fibrous particles".

LF1: particles having an elongation of less than 0.5, an aspect ratio of less than 0.5, and an LEFI (length of fiber) of 200 μm or more, and LF2: particles having an elongation of less than 0.5, an aspect ratio of 0.5 or more, a circularity of less than 0.7, and an LEFI (length of fiber) of 200 μm or more.

The volume ($V_{LF}$) of the long fibrous particles of L-HPC may be calculated by the following equation wherein each long fibrous particle is assumed to be a cylindrical column having a bottom diameter of DIFI and a height of LEFI.

$$V_{LF} = (\pi/4) \times (DIFI)^2 \times (LEFI) \times N_{LF},$$

wherein $N_{LF}$ is the number of long fibrous particles in the sample, DIFI is a median DIFI corresponding to the 50% cumulative value on the number-based cumulative particle diameter distribution curve of long fibrous particles, and LEFI is a median LEFI corresponding to the 50% cumulative value on the number-based cumulative particle diameter distribution curve of long fibrous particles.

The volume of particles satisfying the definition of LF1 and the volume of particles satisfying the definition of LF2 are calculated in accordance with the above equation, respectively, and a sum of these volumes means the volume of the long fibrous particles of L-HPC.

<Short Fibrous Particles>

Particles satisfying the following definition of SF1 or SF2 are divided into "short fibrous particles".

SF1: particles having an elongation of less than 0.5, an aspect ratio of less than 0.5, and an LEFI (length of fiber) of 40 μm or more and less than 200 μm, and SF2: particles having an elongation of less than 0.5, an aspect ratio of 0.5 or more, a circularity of less than 0.7, and an LEFI (length of fiber) of 40 μm or more and less than 200 μm.

The volume ($V_{SF}$) of the short fibrous particles of L-HPC may be calculated by the following equation where each short fibrous particle is assumed to be a cylindrical column having a bottom diameter of DIFI and a height of LEFI, in the same manner as for the above long fibrous particles.

$$V_{SF}=(\pi/4)\times(DIFI)^2\times(LEFI)\times N_{SF},$$

wherein $N_{SF}$ is the number of short fibrous particles in the sample, DIFI is a median DIFI corresponding to the 50% cumulative value on the number-based cumulative particle diameter distribution curve of short fibrous particles, and LEFI is a median LEFI corresponding to the 50% cumulative value on the number-based cumulative particle diameter distribution curve of short fibrous particles.

The volume of particles satisfying the definition of SF1 and the volume of particles satisfying the definition of SF2 are calculated in accordance with the above equation, respectively, and a sum of these volumes means the volume of the short fibrous particles of L-HPC.

<Spherical Particles>

Particles satisfying the definition S1 or S2 is divided into "spherical particles".

S1: particles having an LEFI (length of fiber) of 40 μm or more and an elongation of 0.5 or more, and S2: particles having an LEFI (length of fiber) of 40 μm or more, an elongation of less than 0.5, an aspect ratio of 0.5 or more, and a circularity of 0.7 or more.

The volume ($V_S$) of the spherical particles of L-HPC may be calculated by the folio wing equation, wherein each spherical particle is assumed to be a sphere having a diameter of EQPC.

$$V_S=(\pi/6)\times(EQPC)^3\times N_S,$$

where $N_S$ is the number of spherical particles in the sample, and EQPC is a median EQPC corresponding to the 50% cumulative value on the number-based cumulative particle diameter distribution curve of spherical particles.

The volume of the particles satisfying the definition S1 and the volume of the particles satisfying the definition S2 are calculated in accordance with the above equation, respectively, and a sum of these volumes means the volume of the spherical particles of L-HPC.

The volume fraction of each type of particles of L-HPC may be calculated from the following corresponding equation on basis of the above defined volumes, $V_m$, $V_{LF}$, $V_{SF}$ and $V_S$.

Volume fraction of fine particles=$\{V_m/(V_m+V_{LF}+V_{SF}+V_S)\}\times 100$

Volume fraction of long fibrous particles=$\{V_{LF}/(V_m+V_{LF}+V_{SF}+V_S)\}\times 100$ Volume fraction of short fibrous particles=$\{V_{SF}/(V_m+V_{LF}+V_{SF}+V_S)\}\times 100$ Volume fraction of spherical particles=$\{V_S/(V_m+V_{LF}+V_{SF}+V_S)\}\times 100$ The volume fraction of each type of particles, which are long fibrous particles, short fibrous particles, spherical particles and fine particles, is determined as follows. A dynamic image analysis type particle diameter distribution analyzer QICPIC/R16 (manufactured by Sympatec GmbH) equipped with a quantitative feeder VIBRI/L, an air flow type disperser RODOS/L and an M7 lens is used under the conditions of a frame rate of 500 Hz, an injector of 4 mm, a dispersion pressure of 1 bar. The graphics of the imaged particles are analyzed by analysis software WINDOX5 Version 5.9.1.1 to determine the number-based median EQPC, the number-based median LEFI, the number-based median DIFI, the elongation, the aspect ratio and the circularity with respect to each type of particles. The volume fraction of each type of particles is calculated by the above equation based on the measured values. It is noted that M7 is used as the division of analysis.

The hydroxypropoxy group content of L-HPC is 5.0 to 16.0% by mass, preferably 6.0 to 15.0% by mass, and more preferably 7.0 to 14.0% by mass. When the hydroxypropoxy group content is less than 5.0% by mass, the swelling property of L-HPC becomes low after water absorption. When the hydroxypropoxy group content is more than 16.0% by mass, the water solubility of L-HPC increases, so that the disintegratability becomes insufficient when used in a solid preparation.

The hydroxypropoxy group content of L-HPC may be measured by the assay described in "Low-Substituted Hydroxypropyl cellulose" of the Japanese Pharmacopoeia Seventeenth Edition.

The volume fraction of long fibrous particles of L-HPC is greater than 50.0%, preferably from 51.0 to 100.0%, more preferably from 52.5 to 99.0%, still more preferably from 65.0% to 98.0%, and particularly preferably from 75.0 to 95.0%. When the volume fraction of the long fibrous particles of L-HPC is less than 50%, addition of a small amount of the L-HPC into a solid preparation results in the insufficient bindability, thereby causing capping.

The volume fraction of the short fibrous particles of L-HPC is preferably less than 50.0%, more preferably from 1.0 to 40.0%, still more preferably from 2.0 to 35.0%, and particularly preferably from 3.0 to 25.0%, from the viewpoint of good fluidity, high moldability (bindability) and anti-capping performance of L-HPC.

The volume fraction of the fibrous particles (i.e. a sum of the volume fractions of the long and short fibrous particles) of L-HPC is preferably 80.0% or more, more preferably 82.0 to 100.0%, still more preferably 85.0 to 99.0%, further still more preferably 88.0 to 98.0%, and particularly preferably 90.0 to 98.0%, from the viewpoint of high moldability (bindability) and anti-capping performance of L-HPC.

The volume fraction of the spherical particles of L-HPC is preferably 19.0% or less, more preferably 0.0 to 18.0%, still more preferably 1.0 to 15.0%, and particularly preferably 2.0 to 10.0%, from the viewpoint of high moldability (bindability) and anti-capping performance of L-HPC.

The volume fraction of the fine particles of L-HPC is preferably 20.0% or less, more preferably 0.0 to 10.0%, still more preferably 0.3 to 2.0%, and particularly preferably 0.5 to 1.0%, from the viewpoint of good flowability of L-HPC.

A volume-based $D_{50}$ (median diameter) of L-HPC by dry laser diffractometry is preferably from 30 to 200 μm, more preferably from 70 to 180 μm, still more preferably from 78 to 160 μm, particularly preferably from 90 to 150 μm, and most preferably from 120 to 140 μm, from the viewpoint of disintegrability, moldability (bindability), anti-capping performance and flowability of L-HPC.

A volume-based $D_{90}$ of L-HPC by dry laser diffractometry is preferably from 100 to 500 μm, more preferably from 240 to 480 μm, still more preferably from 260 to 450 μm, particularly preferably from 300 to 430 μm, and most preferably from 340 to 410 μm, from the viewpoint of the disintegrability, moldability (bindability), anti-capping performance and flowability of L-HPC.

The volume-based $D_{50}$ (median diameter) and $D_{90}$ of L-HPC by the dry laser diffraction method are measured in a dry method by using a laser diffraction type particle size distribution analyzer Mastersizer 3000 (produced by Malvern Panalytical Ltd.) with Fraunhofer diffraction theory under the conditions of a dispersion pressure of 2 bar and a scattering intensity of 2 to 10%. In the volume-based cumulative size distribution curve, diameters corresponding to 50% and 90% cumulative values are determined.

The water content (based on weight loss on drying) of L-HPC is preferably 15.0% by mass or less, more preferably 0.1 to 10.0% by mass, from the viewpoint of good bindability, disintegrability and storage stability of the active ingredient when the L-HPC is contained in a preparation.

The water content (based on weight loss on drying) of L-HPC may be measured in accordance with "2.41 Loss on Drying Test" of General Tests cited in "Low-Substituted Hydroxypropyl Cellulose" in the Japanese Pharmacopoeia Seventeenth Edition.

Next, a method for producing the above-described L-HPC will be described.

The L-HPC may be produced by a method comprising steps of bringing a pulp into contact with an alkali metal hydroxide solution to obtain alkali cellulose; reacting the alkali cellulose with propylene oxide to obtain a reaction product mixture containing L-HPC; mixing the reaction product mixture with water and an acid to obtain a precipitate of L-HPC (i.e. crude L-HPC); washing the precipitate to obtain L-HPC; drying the L-HPC to obtain dried L-HPC; and pulverizing and/or sieving the dried L-HPC to obtain L-HPC powder.

First, a pulp and an alkali metal hydroxide solution are brought into contact with each other to obtain alkali cellulose.

Examples of the pulp include pulp derived from wood and pulp derived from cotton linter. The pulp is preferably derived from wood from the viewpoint of the absence of GMO (genetically modified organism). Examples of tree species of the wood may include conifers such as pine, spruce and tsuga, and hardwoods such as eucalyptus and maple. Examples of the shape of the pulp include sheet, chips and powder.

The length-weighted mean width of the pulp is preferably 10 to 40 μm, more preferably 2.5 to 35 μm, from the viewpoint of appropriate facilitation of pulverization in the pulverization step. The length-weighted mean length of the pulp is preferably 0.1 to 3.0 mm from the viewpoint of adjustment efficiency or miscibility with an alkali metal hydroxide solution.

The length-weighted mean width and length-weighted mean length of pulp may be measured by a method (automated optical analysis) in accordance with JIS (Japanese Industrial Standards) P 8226. For example, the measurement may be carried out using a Kayaani fiber length analyzer FS300 (produced by Metso Automation).

Examples of the alkali metal hydroxide include sodium hydroxide and potassium hydroxide. The alkali metal hydroxide is preferably sodium hydroxide from the viewpoint of economy. As the alkali metal hydroxide solution, an aqueous sodium hydroxide solution is preferable. The concentration of the alkali metal hydroxide in the aqueous alkali metal hydroxide solution is preferably 20 to 50% by mass from the viewpoint of uniformity of the alkali cellulose and reaction efficiency.

The alkali cellulose may be subjected to compression to obtain alkali cellulose containing a desired amount of alkali metal hydroxide after bringing pulp into contact with an alkali metal hydroxide solution.

The alkali metal hydroxide content of the alkali cellulose is preferably 5 to 35% by mass from the viewpoint of the reaction efficiency of propylene oxide. The alkali metal hydroxide content of the alkali cellulose may be measured by neutralization titration of the alkali cellulose with an acid (e.g. sulfuric acid) having a known concentration.

The mixing temperature for mixing the pulp with the alkali metal hydroxide solution is preferably 20 to 80° C. The mixing time for mixing the pulp with the alkali metal hydroxide solution is preferably 5 to 120 minutes.

Next, the alkali cellulose is reacted with propylene oxide to obtain a reaction product mixture containing L-HPC.

From the viewpoint of reaction controllability, it is preferable to carry out the reaction in a self-rotating reactor, a reactor with an internal stirrer, or the like, which is preferably capable of adjusting an internal temperature by a jacket. An amount of propylene oxide is preferably 5.5 to 30.0 parts by mass relative to 100 parts by mass of anhydrous pulp from the viewpoint of reaction efficiency of propylene oxide.

The reaction temperature is preferably 40 to 80° C. from the viewpoint of reaction controllability and productivity. The reaction time is preferably 0.5 to 6 hours from the viewpoint of reaction controllability and productivity.

Next, the reaction product mixture is mixed with water and an acid to obtain precipitate of L-HPC (i.e., crude L-HPC).

Mixing may be carried out, for example, in a reactor with an internal stirrer, a jacketed twin-shaft kneader, or the like.

An amount of water is preferably 100 to 1000 parts by mass relative to 100 parts by mass of the alkali cellulose from the viewpoint of solubility of the reaction product (L-HPC). It is noted that the amount of water may be used (or added) at one time, or may be divided and used (or added) at a plurality of times.

Examples of the acid include acetic acid and hydrochloric acid. An amount of the acid is preferably from 95 to 100% of the equivalent of the alkali metal hydroxide contained in the alkali cellulose from the viewpoint of reducing the amount of the alkali metal hydroxide remaining in L-HPC. The acid may be used as it is or as a mixture of the acid and water. The acid is preferably used as a mixture of the acid and water from the viewpoint of avoiding a local neutralization reaction between the reaction product mixture and the acid.

Further, the reaction product mixture may be mixed with an aqueous acid solution containing an acid which is in an amount corresponding to a part of the equivalent amount required to neutralize the alkali metal hydroxide contained in the alkali cellulose, so that a portion of the reaction product may be dissolved. Alternatively, the reaction product mixture may be mixed with an aqueous acid solution containing an acid which is in an amount corresponding to the equivalent amount required to neutralize the alkali metal hydroxide contained in the alkali cellulose may be mixed, so that the reaction product may not be dissolved at all to precipitate L-HPC.

When a portion of the reaction product is dissolved, an aqueous acid solution containing an acid is further added until it reaches the equivalent amount required to neutralize the alkali-metal hydroxide contained in the alkali cellulose to precipitate L-HPC.

The mixing temperature is preferably from 5 to 80° C. from the viewpoint of solubility of the reaction product. The mixing temperature may be controlled by a jacket temperature.

Next, the precipitate of L-HPC is washed to obtain L-HPC.

The washing step may comprise, for example, bringing the precipitate into contact with water to obtain a mixture and then dehydrating the mixture with a dehydrator. The temperature of water to be used for washing is preferably 50° C. or higher from the viewpoint of washability. The amount of water to be used for washing is preferably 1000 to 10000 parts by mass relative to 100 parts by mass of the alkali cellulose from the viewpoint of economical efficiency.

Examples of the dehydrator include a press type dehydrator and a batch type centrifugal dehydrator. The centrifugal effect of the batch type centrifugal dehydrator may be selected for sufficient dehydration, and is preferably a centrifugal acceleration of 500 G or more from the viewpoint of productivity.

Next, L-HPC obtained by washing is dried to obtain dried L-HPC.

The drying may be carried out by using a dryer. Examples of the dryer include a fluidized bed dryer, an air flow dryer, a box type dryer, a vibrating dryer, a natural convection type constant temperature oven, a forced convection constant temperature oven, a forced convection constant temperature constant humidity oven, and a shelf dryer. The drying temperature may be preferably from 60 to 120° C. from the viewpoint of drying efficiency. The drying time may be preferably from 0.5 to 36 hours from the viewpoint of productivity.

Next, the dried L-HPC is pulverized and/or sieved to obtain a L-HPC powder.

The pulverization may be carried out using a pulverizer. Examples of the pulverizer preferably include an impact type pulverizer such as a hammer mill, an impact mill and a victory mill. The screen diameter in the pulverizer may be appropriately selected according to the intended particle size distribution of L-HPC. It is preferably 0.1 mm to 6.0 mm. The pulverization conditions may be appropriately selected according to a type of sieving machine or the intended volume fractions of L-HPC.

The sieving may be carried out using a sieve shaker. Examples of the sieve shaker include a vibration sieving machine, an in-plane motion sieving machine, and a Ro-Tap type sieving machine.

Examples of the vibration sieving machine include ripple flow K and R screens (produced by Kobukuro Techno Co., Ltd.), low head K and R screens (produced by Kobukuro Techno Co., Ltd.), electromagnetic screens (produced by Sinfonia Technology Co., Ltd.), electromagnetic labo sieving machine (produced by Fritsch GmbH), RV screens (produced by Sinfonia Technology Co., Ltd.), balanced screens (produced by Sinfonia Technology Co., Ltd.), BM screens (produced by Sinfonia Technology Co., Ltd.), wave screens (produced by Sinfonia Technology Co., Ltd.), linear drive screens (produced by Sinfonia Technology Co., Ltd.), gyro screens (produced by Sinfonia Technology Co., Ltd.), rubber spring screens (produced by Sinfonia Technology Co., Ltd.), a grizzly feeder (produced by Sinfonia Technology Co., Ltd.), and a circular vibration sieving machine (produced by Dalton Corporation).

Examples of the in-plane motion sieving machine include an aluminum square sifter (produced by Meiji Machine Co., Ltd.), a plan sifter (produced by Meiji Machine Co., Ltd.), a gyratory sifter (produced by Meiji Machine Co., Ltd.), a gyro sifter (produced by TOKUJU CORPORATION), a ROTEX screener (produced by ROTEX Co., Ltd.), and an Allgaier sifter (produced by Allgaier Co., Ltd.).

Examples of the Ro-Tap type sieving machine include a Ro-Tap type sieving shaker (produced by TAKEDA Corporation and Kansai Wire Netting Co., Ltd.), and a BS sieve shaker (produced by SEISHIN ENTERPRISE Co., Ltd.).

An effective sieve area in the sieve is preferably 0.0001 to 1,000 $m^2$, more preferably 0.0010 to 100 $m^2$, from the viewpoint of industrial availability.

The opening of the sieve surface in the sieve may be appropriately selected depending on a purpose. It is preferably from 0.045 to 0.500 mm, more preferably from 0.060 to 0.300 mm, from the viewpoint of the treatment rate, or flowability, disintegratability and bindability of L-HPC.

The line diameter of the sieve surface in the sieve may be appropriately selected depending on a purpose. It is preferably 0.001 to 5.0 mm, more preferably 0.01 to 1.0 mm, from the viewpoint of strength.

The sieving conditions may be appropriately selected depending on a type of sieving machine to be used or the intended volume fractions of L-HPC. As a result, a sieve-passed fraction, a residue on a sieve, or a mixture containing the former and the latter at a desirable ratio may be recovered.

The sieving time of from the start of the sieving of L-HPC to the completion of the sieving of L-HPC, and the time for recovering a sieve-passed fraction or the residue on a sieve, may be appropriately selected according to the intended particle size distribution of L-HPC. They are preferably 0.1 to 12 hours in total from the viewpoint of productivity.

Next, a solid preparation comprising the above-described L-HPC will be described.

Examples of the dosage form of the solid preparation include a tablet, a granule and a fine granule. The tablet is preferable from the viewpoint of easy handling and the most common usage. The granule and the fine granule are obtained by granulating a powdery composition containing L-HPC. The granules or the fine granules may be filled into a capsule.

A solid preparation may optionally comprise an active ingredient and/or an additive.

The active ingredient is not particularly limited as long as it can be orally administered. Examples of the active ingredient include drugs used in pharmaceutical products and active ingredients used in health prods such as foods with nutrient function claims, foods for specified health use, and foods with functional claims. If necessary, two or more types of active ingredients pray be comprised. A commercially available active ingredient may be used.

Example of the drug used in pharmaceutical products include a drug for the central nervous system, a drug for the cardiovascular system, a drug for the respiratory system, a drug for the digestive system, an antibiotic, an antitussive and expectorant, an antihistamine, an antipyretic anti-inflammatory analgesic, a diuretic, an autonomic agent, an antimalarial agent, an antidiarrheal agent, a psychotropic, and vitamins and derivatives thereof.

Examples of the drug for the central nervous system include diazepam, idebenone, naproxen, piroxicam, indomethacin, sulindac, lorazepam, nitrazepam, phenytoin, acetaminophen, ethenzamide, ketoprofen, and chlordiazepoxide.

Examples of the drug for the cardiovascular system include molsidomine, vinpocetine, propranolol, methyldopa, dipyridamole, furosemide, triamterene, nifedipine, atenolol, spironolactone, metoprolol, pindolol, captopril, isosorbide dinitrate, delapril hydrochloride, meclofenoxate hydrochloride, diltiazem hydrochloride, etilefrine hydrochloride, digitoxin, and alprenolol hydrochloride.

Examples of the drug for the respiratory system include amlexanox, dextromethorphan, theophylline, pseudoephedrine, salbutamol, and guaifenesin.

Examples of the drug for the digestive system include a benzimidazole drug having antiulcer action, such as 2-[[3-methyl-4-(2,2,2-trifluoroethoxy)-2-pyridyl]methylsulfinyl]benzimidazole and 5-methoxy-2-[(4-methoxy-3,5-dimethyl-2-pyridyl)methylsulfinyl]benzimidazole; cimetidine; ranitidine; pirenzepine hydrochloride; pancreatin; bisacodyl; and 5-aminosalicylic acid.

Examples of the antibiotic include talampicillin hydrochloride, bacampicillin hydrochloride, cefaclor, and erythromycin.

Examples of the antitussive and expectorant include noscapine hydrochloride, carbetapentane citrate, isoaminile citrate, and dimemorfan phosphate.

Examples of the antihistamine include chlorpheniramine maleate, diphenhydramine hydrochloride, and promethazine hydrochloride.

Examples of the antipyretic anti-inflammatory analgesic include ibuprofen, diclofenac, sodium, flufenamic acid, sulpyrine, aspirin, and ketoprofen.

Examples of the diuretic include caffeine.

Examples of the autonomic agent include dihydrocodeine phosphate, dl-methylephedrine hydrochloride, atropine sulfate, acetylcholine chloride, and neostigmine.

Examples of the antimalarial agent include quinine hydrochloride.

Examples of the antidiarrheal agent include loperamide hydrochloride.

Examples of the psychotropic include chlorpromazine.

Examples of the vitamins and derivatives thereof include vitamin A, vitamin B1, fursultiamine, vitamin B2, vitamin B6, vitamin B12, vitamin C, vitamin D, vitamin E, vitamin K, calcium pantothenate, and tranexamic acid.

Examples of the active ingredient used in the health food include the above vitamins and derivatives thereof, minerals, carotenoids, amino acids and derivatives thereof, plant extracts, and health food materials.

Examples of the mineral include calcium, magnesium, manganese, zinc, iron, copper, selenium, chromium, sulfur, and iodine.

Examples of the carotenoid include β-carotene, α-carotene, lutein, cryptoxanthin, zeaxanthin, lycopene, astaxanthin, and multicarotene.

Examples of the amino acid include an acidic amino acid, a basic amino acid, a neutral amino acid, and an acidic amino acid amide.

Examples of the acidic amino acid include aspartic acid and glutamic acid.

Examples of the basic amino acid include lysine, arginine, and histidine.

Examples of the neutral amino acid include linear aliphatic amino acids such as alanine and glycine; branched aliphatic amino acids such as valine, leucine and isoleucine; hydroxyamino acids such as serine and threonine; sulfur-containing amino acids such as cysteine and methionine; aromatic amino acids such as phenylalanine and tyrosine; heterocyclic amino acids such as tryptophan; and imino acids such as proline.

Examples of the acidic amino acid amide include asparagine and glutamine.

Examples of the amino acid derivative include acetylglutamine, acetylcysteine, carboxymethylcysteine, acetyltyrosine, acetylhydroxyproline, 5-hydroxyproline, glutathione, creatine, S-adenosylmethionine, glycylglycine, glycylglutamine, dopa, alanylglutamine, carnitine and γ-aminobutyric acid.

Examples of the plant extract include aloe extract, propolis extract, agaricus extract, *Panax ginseng* extract, ginkgo leaf extract, turmeric extract, curcumin, sprouted brown rice extract, shiitake mycelium extract, *Rubus suavissimus* extract, sweet Hydrangea leaf extract, *Fomes yucatensis* extract, sesame extract, garlic extract, maca (*Lepidium meyenii*) extract, plant worm (*Cordyceps sinensis*) extract, chamomile extract, and red pepper extract.

Examples of the health food material include royal jelly; dietary fibers; proteins; bifidobacteria; lactic acid bacteria; chitosan; yeast; glucosamine; lecithin; polyphenols; cartilage of animals, fish and shellfish; soft-shelled turtle; lactoferrin; freshwater clams; eicosapentaenoic acid; germanium; enzymes; creatine; carnitine; citric acid; raspberry ketone; coenzyme Q10; methylsulfonylmethane; and soybean peptides bonded with phospholipids.

Examples of the additive include a disintegrant, a binder, an extender, a flavoring ingredient, a fragrance, and a lubricant. If necessary, two or more types of the additive may be comprised. A commercially available additive may be used.

Examples of the disintegrant include cornstarch, potato starch, partially pregelatinized starch, sodium carboxymethyl starch, carmellose, croscarmellose sodium, crystalline cellulose, and crospovidone.

Examples of the binder include hydroxypropyl cellulose, polyvinylpyrrolidone, and hydroxypropyl methyl cellulose.

Examples of the extender include erythritol, mannitol, sorbitol, lactose, sucrose, calcium phosphate, and calcium sulfate.

Examples of the flavoring ingredient include citric acid, tartaric acid, and malic acid.

Examples of the fragrance include menthol, peppermint oil, and vanillin.

Examples of the lubricant include magnesium stearate and sucrose fatty acid esters.

The L-HPC content in the solid preparation is preferably 2 to 50% by mass, more preferably 2 to 30% by mass, and still more preferably 3 to 20% by mass, from the viewpoint of bindability, disintegratability, and storage stability. In particular, when the above-described L-HPC is used, even if the L-HPC content is reduced to preferably 1 to 4.5% by mass, more preferably 1 to 3.5% by mass, good hardness and disintegratability can be imparted to the solid preparation, and capping can be prevented.

The content of the active ingredient in the solid preparation is not particularly limited. It is preferably from 0.05 to 98.95% by mass, more preferably from 0.1 to 97.9% by mass, and still more preferably from 0.5 to 96.5% by mass, from the viewpoint of drug efficacy or effects.

The content of the additive in the solid preparation is preferably from 0.05 to 98.95% by mass, more preferably from 0.1 to 97.9% by mass, and still more preferably from 0.5 to 96.5% by mass, from the vies point of, for example, moldability and disintegratability of the tablet, and/or dissolution of the active ingredient.

A tablet, which is one of solid preparations, may be produced by a method for producing a tablet comprising steps of: mixing L-HPC and an optional active ingredient and/or an optional additive to obtain powder for tableting, and tableting the obtained powder obtain a tablet.

Examples of the tableting include a dry direct tableting, a wet agitation granulation tableting, a fluidized bed granulation tableting, and a dry granulation tableting. The dry direct tableting is preferable from the viewpoint of simpleness of production process, more simplified production process in compared with a wet agitation granulation tableting, and the remarkable reduction of production cost. Tableting may be carried out by using a tableting machine such as a rotary tablet press and a single punch tablet press.

An optional lubricant may be used in the tableting step.

Examples of the lubricant include talc; magnesium stearate; calcium stearate; sodium stearyl fumarate; sucrose fatty acid esters; waxes such as paraffin wax and carnauba wax; and hardened oils such as hardened castor oil, hardened rapeseed oil and hardened beef tallow oil. An amount of the lubricant is preferably 0.05 to 10 parts by mass relative to 100 parts by mass of the powder (excluding the lubricant) for tableting. The lubrication with a lubricant may be external lubrication or internal lubrication.

The tablet diameter is preferably from 3 to 20 mm from the viewpoint of handleability and ingestibility. The tablet weight is preferably from 70 to 700 mg per tablet from the viewpoint of handleability and ingestibility. The tableting pressure during tableting is preferably from 3 to 20 kN from the viewpoint of tablet hardness and reduction of tableting disorder.

EXAMPLES

The invention will be described in detail with reference to Examples and Comparative Examples. It should not be construed that the invention is limited to or by Examples.

Example 1

The 600 g (566 g in terms of anhydrous content) of powdery pulp having a length-weighted mean width of 26 μm and a length-weighted mean length of 0.5 mm derived from pine wood was placed in a reactor having an internal stirrer and an internal volume of 10 L, and subjected to addition of 240 g of a 35% by mass aqueous sodium hydroxide solution, while stirring. Then, the powdery pulp and the aqueous sodium hydroxide solution were mixed at a jacket temperature of 45° C. for 30 minutes to obtain alkali cellulose containing 10% by mass of sodium hydroxide.

Next, the reactor was purged with nitrogen, and 90.6 g of propylene oxide (16.0 parts by mass relative to 100 parts by mass of anhydrous pulp) was added therein and stirred for the reaction at 60° C. for 2 hours to obtain 920 g of reaction product mixture containing L-HPC.

Next, a 2% by mass aqueous acetic acid solution prepared by mixing water with glacial acetic acid was added into the reactor in an amount of 6300 g (100% of the neutralization equivalent) and stirred at a jacket temperature of 60° C. for neutralization to precipitate crude L-HPC.

Thereafter, the crude L-HPC was washed with water of 60° C. (2500 parts by mass relative to 100 parts by mass of alkali cellulose) and dehydrated by using batch-type centrifugal dehydration at a centrifugal acceleration of 1000 G, and then dried at 80° C. for 18 hours in a shelf dryer to obtain the dried L-HPC.

The dried L-HPC was pulverized in an impact mill (Victory Mill VP-1 produced by Hosokawa Micron Ltd.) having a screen diameter of 0.5 mm to obtain pulverized L-HPC.

The whole amount of the pulverized L-HPC was placed into an in-plane motion sieving machine (Gyro-Sifter GS-A1H produced by TOKUJU Corporation), sieved with a 200-mesh sieve (an effective sieve area of 0.14 m$^2$, mesh opening of 77 μm, a wire diameter of 50 μm, product of Kansai Wire Netting Co., Ltd.) for 20 minutes. The sieve-passed fraction was collected to obtain L-HPC having a water content (based on weight loss on drying) of 2.0% by mass.

The obtained L-HPC was subjected to the measurement of the hydroxypropoxy group content, a median diameter ($D_{50}$), $D_{90}$ and volume fractions of various shapes of particles (long fibrous particles, short fibrous particles, spherical particles and fine particles). The results are shown in Table 1.

<Tablet Evaluation>

(1) Production of Acetaminophen Tablet

The 490 g of acetaminophen (fine powder grade, produced by Yamamoto Chemical Industry Co., Ltd.) was placed in a fluidized bed granulator (Multiplex MP-01, produced by Powrex Corporation) and granulated, while spraying 200 g of a 5% by mass aqueous solution of hydroxypropyl methyl cellulose (hydroxypropoxy group content of 8.8% by mass, methoxy group content of 29.0% by mass, and viscosity at 20° C. of 3.0 mPa·s as determined in a 2% by mass aqueous solution) thereto, under the following conditions: an intake air temperature of 60° C., an air flow of 0.5 to 0.7 m$^3$/min, an exhaust gas temperature of 30 to 35° C., a spray air pressure of 200 kPa, and a spray rate of 10 g/min. Subsequently, the granulation product was dried until the exhaust gas temperature became 45° C., and then passed through a sieve having mesh opening of 500 μm to obtain acetaminophen granules containing 98% by mass of acetaminophen.

The 95 to 97 parts by mass of the obtained acetaminophen granules were mixed with 3 to 5 parts by mass of L-HPC to make a total amount 100 parts by mass to obtain powder for tableting. Next, the powder for tableting was mixed with 1.0 parts by mass of magnesium stearate as a lubricant, and tableted with a rotary tableting machine (VIRGO, produced by Kikusui Seisakusho Ltd.) at a tableting pressure of 10 kN and a tableting speed of 20 rpm to produce an acetaminophen tablet having a diameter (tablet diameter) of 8 mm, a radius of curvature of 6.5 mm, and tablet mass of 200 mg.

(2) Production of Glucosamine Tablets

Further, 40 parts by mass of glucosamine (Koyo glucosamine SC, produced by Koyo Chemical Co., Ltd.) was mixed with 57 parts by mass of lactose (Dilactose S, produced by Freund Corporation) and 3 parts by mass of L-HPC as a second formulation to obtain powder for tableting. Next, the powder for tableting was mixed with 0.5 parts by mass of magnesium stearate as a lubricant, and tableted by using a rotary tableting machine (VIRGO, produced by Kikusui Seisakusho Ltd.) at a tableting pressure of 12 kN and a tableting speed of 20 rpm to produce a glucosamine tablet having a diameter (tablet diameter) of 8 mm, a radius of curvature of 6.5 mm, and tablet mass of 300 mg.

(3) Evaluation of Capping Occurrence Ratio

The capping occurrence ratio of the obtained tablets was evaluated. The results are shown in Table 1. The capping occurrence ratio of the tablets was obtained by placing 50 tablets in a drum of a friability tester (TA, produced by ERWEKA GmbH); rotating the drum at 25 rpm 500 times for 20 minutes; and then counting the number of tablets in which capping occurred, that is, the number of tablets having division into two layers for calculating the capping occurrence ratio by the following formula.

Capping occurrence ratio (%)={(number of tablets having capping occurred)/50}×100

(4) Evaluation of Tablet Hardness and Disintegration Time

The hardness and disintegration time of the acetaminophen tablets and the glucosamine tablets were evaluated. The results are shown in Table 1. The hardness of the tablet was measured as the maximum breaking strength when the tablet was broken by applying a load at a rate of 1 mm/sec in the diameter direction of the tablet using a tablet hardness tester (TBH-125, produced by ERWEKA GmbH). The disintegration time of the tablet was measured using a tablet disintegration tester (NT-400, produced by Toyama Sangyo Co., Ltd.) in accordance with the disintegration test method (test solution: water, without disks) of the Japanese Pharmacopoeia Seventeenth Edition.

Example 2

L-HPC having a water content (based on weight loss on drying) of 2.0% by mass was produced in the same manner as in Example 1 except that the dried L-HPC was pulverized in an impact mill (Victoria mill VP-1, produced by Hosokawa Micron Ltd.) having a screen diameter of 0.3 mm, and then sieved with a 100 mesh sieve (an effective sieve area of 0.14 m$^2$, mesh opening of 154 μm, a wire diameter of 100 μm, Kansai Wire Netting Co., Ltd.) for 20 minutes; and the sieve-passed fraction was further sieved with a 350 mesh sieve (an effective sieve area of 0.14 m$^2$, mesh opening of 38 μm, a wire diameter of 35 μm, Kansai Wire Netting Co., Ltd.) for 20 minutes to recover the residue on the sieve. The hydroxypropoxy group content, the median diameter ($D_{50}$), $D_{90}$, volume fractions of the various shapes of particles (long fibrous particles, short fibrous particles, spherical particles and fine particles), and a capping occurrence ratio, hardness and disintegration time of tablets were measured in the same manner as in Example 1. The results are shown in Table 1.

Example 3

L-HPC having a water content (based on weight loss on drying) of 2.5% by mass was produced in the same manner as in Example 1 except that a powdery pulp having a length-weighted mean width of 30 μm and a length-weighted mean length of 0.5 mm derived from pine tree wood was used in the reaction; the dried L-HPC was pulverized by an impact mill (Victory Mill VP-1, produced by Hosokawa Micron Ltd.) having a screen diameter of 0.3 mm, and then sieved with a 100 mesh sieve (an effective sieve area of 0.14 m$^2$, mesh opening of 154 μm, a wire diameter of 100 μm, Kansai Wire Netting Co., Ltd.) for 20 minutes to collect the sieve-passed fraction. The capping occurrence ratio, hardness and disintegration time of the tablets were evaluated in the same manner as in Example 1. The results are shown in Table 1.

Example 4

L-HPC having a water content (based on weight loss on drying) of 2.0% by weight was produced in the same manner as in Example 1 except that the dried L-HPC was pulverized in an impact mill (Victory Mill VP-1, produced by Hosokawa Micron Ltd.) having a screen diameter of 0.5 mm, and sieved with a 350 mesh sieve (an effective sieve area of 0.14 m$^2$, mesh opening of 38 μm, a wire diameter of 35 μm, produced by Kansai Wire Netting Co., Ltd.) for 20 minutes to collect the residue on the sieve. The hydroxypropoxy group content, a median diameter ($D_{50}$), $D_{90}$, and volume fractions of various shapes of particles (long fibrous particles, short fibrous particles, spherical particles and fine particles), and hardness and disintegration time of tablets were evaluated in the same manner as in Example 1. The results are shown in Table 1.

Example 5

L-HPC having a water content (based on weight loss on drying) of 2.0% by mass was produced in the same manner as in Example 1 except that the dried L-HPC was, after pulverization, sieved with a 80 mesh sieve (an effective sieve area of 0.14 m$^2$, mesh opening of 198 μm, a wire diameter of 120 μm, produced by Kansai Wire Netting Co., Ltd.) for 20 minutes; and the sieve-passed fraction was further sieved with a 350 mesh sieve (an effective sieve area of 0.14 m$^2$, mesh openings of 38 μm, a wire diameter of 35 μm, produced by Kansai Wire Netting Co., Ltd.) for 20 minutes to collect the residue on the sieve. The capping occurrence ratio, hardness and disintegration time of the tablets were evaluated in the same manner as in Example 1. The results are shown in Table 1.

Example 6

The dried L-HPC obtained in the same manner as in Example 3 was sieved with a 200 mesh sieve (an effective sieve area of 0.14 m$^2$, mesh opening of 77 μm, a wire diameter of 50 μm, produced by Kansai Wire Netting Co., Ltd.) for 20 minutes to collect the residue on the sieve for obtaining L-HPC having a water content (based on weight loss on drying) of 2.5% by mass. The capping occurrence ratio, hardness and disintegration time of the tablets were evaluated in the same manner as in Example 1. The results are shown in Table 1.

Example 7

L-HPC having a water content (based on weight loss on drying) of 2.7% by mass was produced in the same manner as in Example 2 except that the amount of propylene oxide was changed to 65.7 g (11.6 parts by mass relative to 100 parts by mass of anhydrous wood pulp). The capping occurrence ratio, hardness and disintegration time of the tablets were evaluated in the same manner as in Example 1. The results are shown in Table 1.

Example 8

L-HPC having a water content (based on weight loss on drying) of 2.1% by mass was produced in the same manner as in Example 2 except that the amount of propylene oxide was changed to 121 g (21.6 parts by mass relative to 100 parts by mass of anhydrous wood pulp). The capping occurrence ratio, hardness and disintegration time of the tablets were evaluated in the same manner as in Example 1. The results are shown in Table 1.

Comparative Example 1

L-HPC having a water content (based on weight loss on drying) of 2.0% by mass was produced in the same manner as in Example 2 except that the dried L-HPC was pulverized, and sieved with a 100 mesh sieve (an effective sieve area of 0.14 $m^2$, mesh opening of 154 μm, a wire diameter of 100 μm, produced by Kansai Wire Netting Co., Ltd.) for 20 minutes to recover the sieve-passed fraction. The capping occurrence ratio, hardness and disintegration tithe of the tablets were evaluated in the same manner as in Example 1. The results are shown in Table 1.

Comparative Example 2

The 324 g (300 g in terms of anhydrous content) of sheet-like pulp having a length-weighted mean length of 2.56 mm and a length-weighted mean width of 26 μm derived from pine wood was immersed in a 43% by mass aqueous sodium hydroxide solution and then compressed to obtain 663 g of alkali cellulose containing 22.0% by mass of sodium hydroxide.

The obtained alkaline cellulose was placed in a self-rotation type reactor having an internal volume 5 L, then the reactor was purged with nitrogen, and 77 g (25.7 parts by mass relative to 100 parts by mass of anhydrous wood pulp) of propylene oxide was placed in the reactor. The alkali cellulose was reacted with the propylene oxide with stirring at a jacket temperature of 50° C. for 2 hours followed by 60° C. for 1 hours to obtain 740 g of a reaction product mixture containing L-HPC.

Next, the reaction product mixture containing L-HPC, and 199 g (30% of neutralization equivalent) of an 33% by mass aqueous acetic acid solution prepared by mixing glacial acetic acid with water were placed in a kneader reactor. The reaction product mixture containing L-HPC was dispersed in the aqueous acetic acid solution, and then stirred at a jacket temperature of 45° C. for 40 minutes to dissolve a part of L-HPC.

Thereafter, 464 g (70% of neutralization equivalent) of an 33% by mass aqueous acetic acid solution prepared by mixing glacial acetic acid with water was added to the reaction product mixture for complete neutralization to precipitate crude L-HPC.

The crude L-HPC precipitate was dispersed in 3000 parts by weight of hot water of about 90° C., washed and dehydrated with a batch-type centrifugal separator at a centrifugal acceleration rate of 1000 G, and dried in a shelf dryer at 80° C. for 18 hours to obtain dried L-HPC.

The dried L-HPC was pulverized with an impact mill (Victory Mill VP-1, produced by Hosokawa Micron Ltd.) having a 0.3-mm screen.

The whole amount of the pulverized product was placed in an in-plane motion sieving machine (Gyro-Sifter GS-A1H, produced by TOKUJU Corporation), and sieved with a 100 mesh sieve (an effective sieve area of 0.14 $m^2$, mesh opening of 154 μm, a wire diameter of 100 μm, produced by Kansai Wire Netting Co., Ltd.) for 20 minutes to collect the sieve-passed fraction for obtaining L-HPC having a water content (based on weight loss on drying) of 2.1% by weight. The capping occurrence ratio, hardness and disintegration time of the tablets were evaluated in the same manner as in Example 1. The results are shown in Table 1.

TABLE 1

| | L-HPC | | | | | | | acetaminophen tablets | | | | | | | | |
|---|---|---|---|---|---|---|---|---|---|---|---|---|---|---|---|---|
| | | | volume fraction (%) | | | | | | | | | | | | | |
| | HPO group content | particle diameter distribution | | long fibrous particles A | short fibrous particles B | spherical particles | fine particles | A + B | capping occurrence ratio (%) L-HPC content | | | hardness (N) L-HPC content | | | disintegration time (sec) L-HPC content | | |
| | (mass %) | D50 (μm) | D90 (μm) | | | | | | 3 (pbm) | 4 (pbm) | 5 (pbm) | 3 (pbm) | 4 (pbm) | 5 (pbm) | 3 (pbm) | 4 (pbm) | 5 (pbm) |
| Example 1 | 11 | 73 | 261 | 51.2 | 29.4 | 18.9 | 0.5 | 80.6 | 32 | 10 | 0 | 50 | 56 | 77 | 370 | 236 | 154 |
| Example 2 | 11 | 88 | 266 | 54.5 | 27.8 | 17.4 | 0.2 | 82.3 | 26 | 0 | 0 | 50 | 52 | 80 | 365 | 249 | 156 |
| Example 3 | 11 | 88 | 325 | 62.0 | 22.6 | 14.8 | 0.5 | 84.7 | 18 | 0 | 0 | 51 | 52 | 81 | 359 | 241 | 150 |
| Example 4 | 11 | 123 | 233 | 72.5 | 16.5 | 11.0 | 0.0 | 89.0 | 0 | 0 | 0 | 58 | 64 | 85 | 355 | 250 | 158 |
| Example 5 | 11 | 131 | 370 | 80.7 | 10.3 | 9.0 | 0.0 | 91.0 | 0 | 0 | 0 | 62 | 68 | 94 | 362 | 268 | 156 |
| Example 6 | 11 | 140 | 405 | 93.8 | 3.2 | 3.0 | 0.0 | 97.0 | 0 | 0 | 0 | 64 | 72 | 105 | 394 | 305 | 191 |
| Example 7 | a | 90 | 271 | 56.3 | 26.3 | 17.2 | 0.2 | 82.6 | 24 | 0 | 0 | 51 | 63 | 82 | 388 | 279 | 196 |
| Example 8 | 14 | 87 | 262 | 53.6 | 28.1 | 18.0 | 0.3 | 81.7 | 30 | 0 | 0 | 50 | 60 | 79 | 359 | 222 | 142 |
| Comp. Ex. 1 | 11 | 70 | 240 | 40.8 | 55.1 | 23.1 | 1.0 | 75.9 | 48 | 20 | 8 | 38 | 54 | 58 | 302 | 220 | 149 |
| Comp. Ex. 2 | 11 | 64 | 236 | 45.2 | 33.9 | 19.1 | 1.8 | 79.1 | 40 | 14 | 4 | 42 | 55 | 61 | 312 | 240 | 158 |

TABLE 1-continued

|  | glycosamine tablets | | |
|---|---|---|---|
|  | capping occurrence ratio (%) | hardness (N) | disintegration time (sec) |
|  | L-HPC content | | |
|  | 3 (pbm) | 3 (pbm) | 3 (pbm) |
| Example 1 | 30 | 76 | 83 |
| Example 2 | 24 | 76 | 70 |
| Example 3 | 10 | 79 | 78 |
| Example 4 | 0 | 84 | 88 |
| Example 5 | 0 | 98 | 82 |
| Example 6 | 0 | 90 | 93 |
| Example 7 | 22 | 78 | 80 |
| Example 8 | 24 | 76 | 69 |
| Comp. Ex. 1 | 44 | 71 | 85 |
| Comp. Ex. 2 | 38 | 73 | 93 |

"HPO group content" means hydroxypropoxy group content.
"pbm" means parts by mass.

From the results of Examples 1 and Comparative Examples 1 and 2, it is found that, when a tablet (as a solid preparation) containing a L-HPC having a volume fraction of long fibrous particles of more than 50.0% is produced and evaluated, a capping occurrence ratio is reduced.

Further, from the results of Examples 1 to 8, it is found that as the volume fraction of long fibrous particles in L-HPC increases, and as the amount of the L-HPC increases, the advantageous effects are further enhanced. In addition, from the results of Examples 7 and 8, the same advantageous effects are confirmed with respect to L-HPC having different contents of hydroxypropoxy groups.

In addition, it is found that, with respect to the hardness of the tablet, a higher value of hardness can be obtained as the volume fraction of long fibrous particles in L-HPC increases and as the amount of the L-HPC increases. As for the disintegration time, as the amount of the L-HPC increases, disintegration is observed in a short period of time. It is surprisingly found that as the volume fraction of long fibrous particles in L-HPC increases, the same degree of rapid disintegration is observed regardless of the volume fraction of long fibrous particles of L-HPC, despite exhibiting high tablet moldability. This can be attributed to the fact that long fibrous particles with strong swelling power are contained at a high volume fraction in L-HPC.

The invention claimed is:

1. Low-substituted hydroxypropyl cellulose that is in a form of particles, wherein the low-substituted hydroxypropyl cellulose has a hydroxypropoxy group content of 5 to 16% by mass;
   wherein the particles are classified, on a basis of dynamic image analysis, into fine particles, spherical particles, long fibrous particles, and short fibrous particles;
   wherein a volume fraction of the long fibrous particles is more than 50.0% relative to all of the particles; and
   wherein:
   the fine particles have a length of fiber of less than 40 μm;
   the spherical particles have a length of fiber of 40 μm or more and consist of first and second spherical particles, wherein the first spherical particles have an elongation, which is a ratio of a diameter of fiber to a length of fiber, of 0.5 or more, and the second spherical particles have an elongation of less than 0.5, an aspect ratio, which is a ratio of a minimum Feret diameter to a maximum Feret diameter, of 0.5 or more, and a circularity, which is a ratio of a perimeter ($P_{EQPC}$) of a circle that has the same area as a projection area of a particle to a real perimeter ($P_{real}$) of a particle, of 0.7 or more;
   the long fibrous particles have a length of fiber of 200 μm or more and an elongation of less than 0.5, and consist of first and second long fibrous particles, wherein the first long fibrous particles have an aspect ratio of less than 0.5, and the second long fibrous particles have an aspect ratio of 0.5 or more and a circularity of less than 0.7; and
   the short fibrous particles have a length of fiber of 40 μm or more and less than 200 μm and an elongation of less than 0.5, and consist of first and second short fibrous particles, wherein the first short fibrous particles have an aspect ratio of less than 0.5, and the second short fibrous particles have an aspect ratio of 0.5 or more and a circularity of less than 0.7.

2. The low-substituted hydroxypropyl cellulose according to claim 1, wherein a volume fraction of fibrous particles consisting of the long fibrous particles and the short fibrous particles is 80.0% or more.

3. The low-substituted hydroxypropyl cellulose according to claim 1, wherein a volume fraction of the spherical particles is 19.0% or less.

4. A solid preparation comprising the low-substituted hydroxypropyl cellulose of claim 1.

5. The solid preparation according to claim 4, wherein the solid preparation is a tablet.

6. The low-substituted hydroxypropyl cellulose according to claim 2, wherein a volume fraction of the spherical particles is 19.0% or less.

7. A solid preparation comprising the low-substituted hydroxypropyl cellulose of claim 2.

8. The solid preparation according to claim 7, wherein the solid preparation is a tablet.

9. A solid preparation comprising the low-substituted hydroxypropyl cellulose of claim 3.

10. The solid preparation according to claim 9, wherein the solid preparation is a tablet.

11. A solid preparation comprising the low-substituted hydroxypropyl cellulose of claim 6.

12. The solid preparation according to claim 11, wherein the solid preparation is a tablet.

* * * * *

UNITED STATES PATENT AND TRADEMARK OFFICE
CERTIFICATE OF CORRECTION

PATENT NO. : 11,166,918 B2
APPLICATION NO. : 16/993375
DATED : November 9, 2021
INVENTOR(S) : Oguro et al.

It is certified that error appears in the above-identified patent and that said Letters Patent is hereby corrected as shown below:

In the Specification

Column 13, Line 28: Please correct "0.05 to 10 parts" to read -- 0.05 to 2.0 parts --

Columns 17-20, Table 1: Please delete Table 1 and replace with the following:

Signed and Sealed this
Twenty-eighth Day of June, 2022

Katherine Kelly Vidal
*Director of the United States Patent and Trademark Office*

TABLE 1

| | L-HPC | | | | | | | | acetoaminophen tablets | | | | | | | | | glycosamine tablets | | |
|---|---|---|---|---|---|---|---|---|---|---|---|---|---|---|---|---|---|---|---|---|
| | HPO group content | particle diameter distribution | | volume fraction (%) | | | | A+B | capping occurrence ratio (%) | | | hardness (N) | | | disintegration time (sec) | | | capping occurrence ratio (%) | hardness (N) | disintegration time (sec) |
| | | $D_{50}$ | $D_{90}$ | long fibrous particles A | short fibrous particles B | spherical particles | fine particles | | L-HPC content | | | L-HPC content | | | L-HPC content | | | L-HPC content | L-HPC content | L-HPC content |
| | (mass%) | (μm) | (μm) | | | | | | 3 (pbm) | 4 (pbm) | 5 (pbm) | 3 (pbm) | 4 (pbm) | 5 (pbm) | 3 (pbm) | 4 (pbm) | 5 (pbm) | 3 (pbm) | 3 (pbm) | 3 (pbm) |
| Example1 | 11 | 78 | 261 | 51.2 | 29.4 | 18.9 | 0.5 | 80.6 | 32 | 10 | 0 | 50 | 58 | 77 | 370 | 236 | 154 | 30 | 76 | 83 |
| Example2 | 11 | 88 | 266 | 54.5 | 27.8 | 17.4 | 0.3 | 82.3 | 28 | 0 | 0 | 50 | 62 | 80 | 365 | 249 | 156 | 24 | 76 | 70 |
| Example3 | 11 | 88 | 325 | 62.0 | 22.6 | 14.8 | 0.5 | 84.7 | 18 | 0 | 0 | 51 | 62 | 81 | 359 | 241 | 150 | 10 | 79 | 78 |
| Example4 | 11 | 123 | 335 | 72.5 | 16.5 | 11.0 | 0.0 | 89.0 | 0 | 0 | 0 | 58 | 64 | 85 | 355 | 250 | 158 | 0 | 84 | 88 |
| Example5 | 11 | 131 | 370 | 80.7 | 10.3 | 9.0 | 0.0 | 91.0 | 0 | 0 | 0 | 62 | 68 | 94 | 362 | 268 | 166 | 0 | 88 | 82 |
| Example6 | 11 | 140 | 405 | 93.8 | 3.2 | 3.0 | 0.0 | 97.0 | 0 | 0 | 0 | 64 | 72 | 105 | 394 | 305 | 191 | 0 | 90 | 93 |
| Example7 | 8 | 90 | 271 | 56.3 | 26.3 | 17.2 | 0.2 | 82.6 | 24 | 0 | 0 | 51 | 63 | 82 | 388 | 279 | 198 | 22 | 78 | 80 |
| Example8 | 14 | 87 | 262 | 53.6 | 28.1 | 18.0 | 0.3 | 81.7 | 30 | 0 | 0 | 50 | 60 | 79 | 359 | 222 | 142 | 24 | 76 | 69 |
| Comp.Ex.1 | 11 | 70 | 240 | 40.8 | 35.1 | 23.1 | 1.0 | 75.9 | 48 | 20 | 8 | 38 | 54 | 58 | 302 | 220 | 149 | 44 | 71 | 85 |
| Comp.Ex.2 | 11 | 64 | 236 | 45.2 | 33.9 | 19.1 | 1.8 | 79.1 | 40 | 14 | 4 | 42 | 55 | 61 | 312 | 240 | 158 | 38 | 73 | 83 |

\* "HPO group content" means hydroxypropoxy group content.

\* "pbm" means parts by mass.